(12) United States Patent
Takaki et al.

(10) Patent No.: US 8,420,662 B2
(45) Date of Patent: Apr. 16, 2013

(54) STABLE SOLID PREPARATION CONTAINING 4,5-EPOXYMORPHINAN DERIVATIVE

(75) Inventors: Suguru Takaki, Kanagawa (JP); Kotoe Ohta, Kanagawa (JP); Yasuhide Horiuchi, Kanagawa (JP); Masato Kobayashi, Kyoto (JP); Junko Kawasaki, Kyoto (JP); Eijiro Horisawa, Kyoto (JP)

(73) Assignee: Toray Industries, Inc., Tokyo (JP)

( * ) Notice: Subject to any disclaimer, the term of this patent is extended or adjusted under 35 U.S.C. 154(b) by 609 days.

(21) Appl. No.: 12/597,475

(22) PCT Filed: Apr. 25, 2008

(86) PCT No.: PCT/JP2008/058111
§ 371 (c)(1),
(2), (4) Date: Oct. 23, 2009

(87) PCT Pub. No.: WO2008/133330
PCT Pub. Date: Nov. 6, 2008

(65) Prior Publication Data
US 2010/0120815 A1    May 13, 2010

(30) Foreign Application Priority Data
Apr. 26, 2007   (JP) ................. 2007-116721

(51) Int. Cl.
*A61K 31/44*  (2006.01)
*A61K 9/00*   (2006.01)
*A61K 9/16*   (2006.01)
*A61K 9/20*   (2006.01)

(52) U.S. Cl.
USPC .......... 514/282; 424/494; 424/490; 424/400; 424/464

(58) Field of Classification Search ............ None
See application file for complete search history.

(56) References Cited

U.S. PATENT DOCUMENTS

| 5,387,420 A | 2/1995 | Mitchell |
| 6,174,891 B1 | 1/2001 | Nagase et al. |
| 6,299,904 B1 * | 10/2001 | Shimizu et al. ............. 424/464 |
| 6,372,755 B2 * | 4/2002 | Hanamura et al. .......... 514/282 |
| 6,559,134 B2 | 5/2003 | Tanno et al. |
| 2001/0004637 A1 | 6/2001 | Hanamura et al. |
| 2002/0058714 A1 * | 5/2002 | Maruyama ................. 514/781 |
| 2004/0121006 A1 | 6/2004 | Narita et al. |
| 2005/0008698 A1 * | 1/2005 | Maruyama ................. 424/465 |
| 2005/0208127 A1 * | 9/2005 | Ogasawara et al. ........ 424/464 |

FOREIGN PATENT DOCUMENTS

| EP | 0948965 A1 * | 10/1998 |
| JP | 2-160719 A | 6/1990 |
| JP | 11-43429 A | 2/1999 |
| JP | 2001-328948 A | 11/2001 |
| JP | 2002-104956 A | 4/2002 |
| JP | 3531170 B2 | 5/2004 |
| JP | 2005-2123 A | 1/2005 |
| JP | 2005-531515 A | 10/2005 |
| JP | 2006-522818 A | 10/2006 |
| WO | WO-98/23290 A1 | 6/1998 |
| WO | WO-98/35679 A1 | 8/1998 |
| WO | WO-99/02158 A1 | 1/1999 |
| WO | WO-01/76565 A1 | 10/2001 |
| WO | WO-02/070013 A1 | 9/2002 |
| WO | WO-03/077867 A2 | 9/2003 |
| WO | WO-03/103713 A1 | 12/2003 |
| WO | WO-2004/091623 A1 | 10/2004 |

OTHER PUBLICATIONS

U.S. Appl. No. 13/125,726, filed Apr. 2011, Ohta et al.*
Edited by Japan Pharmaceutical Excipients Council, "Iyakuhin Tenkabutsu Jiten, 1st Edition", Yakuji Nippon Ltd., Jan. 14, 1994, pp. 85, 106.

* cited by examiner

*Primary Examiner* — Shengjun Wang
*Assistant Examiner* — Svetlana M Ivanova
(74) *Attorney, Agent, or Firm* — Birch, Stewart, Kolasch & Birch, LLP

(57) ABSTRACT

It is an object of the present invention to provide a stable solid preparation comprising a 4,5-epoxymorphinan derivative or a pharmacologically acceptable acid addition salt thereof as an effective ingredient.
That is, the present invention provides the stable solid preparation comprising the 4,5-epoxymorphinan derivative or the pharmacologically acceptable acid addition salt thereof as the effective ingredient, and comprising sodium thiosulfate, a sugar or a sugar alcohol and hydroxypropylcellulose having a low degree of substitution in an amount of 1 to 30% by weight per weight of a unit containing the effective ingredient.

7 Claims, No Drawings

STABLE SOLID PREPARATION CONTAINING 4,5-EPOXYMORPHINAN DERIVATIVE

TECHNICAL FIELD

The present invention relates to a stable solid preparation comprising a 4,5-epoxymorphinan derivative or a pharmacologically acceptable acid addition salt thereof. More particularly, the present invention relates to a stable solid preparation containing a 4,5-epoxymorphinan derivative or a pharmacologically acceptable acid addition salt thereof as an effective ingredient; sodium thiosulfate, a sugar or a sugar alcohol; and hydroxypropylcellulose having a low degree of substitution in an amount of 1 to 30% by weight per weight of a unit containing the effective ingredient.

The unit containing the effective ingredient here indicates a unit of a solid ingredient being directly contacted with the effective ingredient in the preparation, and for example, is a core tablet in the case of a film-coating tablet, a filled solid ingredient in which a drug is supported and dispersed in the case of a capsule and a core granule in the case of a granule coated with a functional film, which refers to an essential portion that governs a stability of the drug.

BACKGROUND ART

The 4,5-epoxymorphinan derivative represented by the general formula (I) or the pharmacologically acceptable acid addition salt thereof that is the effective ingredient of the present invention has a remarkable antipruritic effect, and has been disclosed as an effective compound for a drug of treating pruritus in various diseases associated with the pruritus (e.g., see patent Document 1 [U.S. Pat. No. 3,531,170]). However, it has been known that the 4,5-epoxymorphinan derivative is chemically unstable to light, heat and oxygen (e.g., see Patent Document 2 [International Publication WO99/02158 Pamphlet]). Therefore, it has been necessary to develop a preparation having the good stability in order to assure its quality.

Conventionally, as methods for stabilizing various morphinan compounds including morphine, a technique of adding a basic ingredient to morphine (e.g., see Patent Document 3 [JP Hei-2-160719-A]), methods of combining an antioxidant such as sodium thiosulfate and tocopherol with naloxone (e.g., Patent Document 4 [International Publication WO98/35679 Pamphlet]), methods of adding a chelating agent and a citrate buffer to methylnaltrexone (e.g., see Patent Document 5 [JP 2006-522818]) and methods of blending an organic acid and a chelate forming agent to naltrexone hydrochloride (e.g., see Patent Document 6 [JP 2005-531515]) have been disclosed. However, these reports do not describe a stabilization effect of hydroxypropylcellulose having a low degree of substitution, which is a particular disintegrant, and it does not necessarily perform such an effect. The technique of stabilizing the 4,5-epoxymarphinan derivative has been disclosed in detail in Patent Document 2, and it has been described that a stable pharmaceutical composition is obtained by containing sugars or sugar alcohols, an antioxidant such as sodium thiosulfate, or the like. However, nothing is described for types and blended amounts of disintegrants and binders that are effective for the stabilization; thus, the stabilization effect given to a solid preparation by hydroxypropylcellulose having the low degree of substitution, which is the particular disintegrant, has not been revealed.

Meanwhile, an orally disintegrating tablet that can be taken without water, which aims at improving a dosing compliance, has been disclosed as the solid preparation containing sugars or sugar alcohols such as lactose, mannitol or erythritol and containing hydroxypropylcellulose having the low degree of substitution as the disintegrant. The following have been disclosed: a composition that contains the effective ingredient, the sugar alcohols and hydroxypropylcellulose having the low degree of substitution, having the degree of substitution and a bulk density of a particular hydroxypropoxyl group and enhances a disintegrating property (e.g., see Patent Document 7 [JP Hei-11-43429-A], Patent Document 8 [JP 2001-328948-A]); or an external lubricant tableting method in which the amount of added magnesium stearate is minimized in order to shorten a disintegrating time in an oral cavity (e.g., see Patent Document 9 [International Publication WO2003/103713 Pamphlet]); the technique that defines an ethanol permeation speed in a lubricant (e.g., see Patent Document 10 [International Publication WO2001/076565 Pamphlet]). However, the solid preparation of the present invention need not be disintegrated in the oral cavity, and thus is essentially different from these problems. More importantly, these reports do not describe sodium thiosulfate, and do no describe its effect on stabilization; therefore, the present invention can not be conceived easily from these reports.

Meanwhile, a technique of preventing degradation of the drug or functional change of functional particles due to compression by using spray dry powders containing the sugar alcohol has been disclosed (e.g., see Patent Document 11 [International Publication WO2002/070013 Pamphlet).

However, in the above report, sodium thiosulfate is not described, and the stabilization effect given to a storage stability of the drug by addition of the sugar alcohol or sodium thiosulfate is not described at all.

Patent Document 1: U.S. Pat. No. 3,531,170
Patent Document 2: International Publication WO99/02158 Pamphlet
Patent Document 3: JP Hei-2-160719-A
Patent Document 4: International Publication WO98/35679 Pamphlet
Patent Document 5: JP 2006-522818
Patent Document 6: JP 2005-531515
Patent Document 7: JP Hei-11-43429-A
Patent Document 8: JP 2001-328948-A
Patent Document 9: International Publication WO2003/103713 Pamphlet
Patent Document 10: International Publication WO2001/076565 Pamphlet
Patent Document 11: International Publication WO2002/070013 Pamphlet

DISCLOSURE OF INVENTION

Problem to be Solved by the Invention

It is an object of the present invention to provide a stable solid preparation comprising a 4,5-epoxymorphinan derivative or a pharmacologically acceptable acid addition salt thereof as an effective ingredient.

Means for Solving the Problem

It was studied to formulate the 4,5-epoxymorphinan derivative represented by the general formula (I) or the pharmacologically acceptable acid addition salt thereof into a solid preparation. As a result, although the method for stabilization by adding an antioxidant such as sodium thiosulfate known conventionally (e.g., see Patent Document 2) was demonstrated to be effective for the stabilization of the effective ingredient in a liquid state, when this method was utilized for the solid preparation, it was found to be difficult to minimize degrading and keep the stability sufficient as the solid preparation in an unpacked state or an ordinary packed state over a long period of time.

Thus, the present inventors have studied extensively to develop the stable solid preparation comprising the 4,5-epoxymorphinan derivative represented by the general formula (I) or the pharmacologically acceptable acid addition salt thereof, and have obtained a finding that the remarkable stabilization effect is obtained by making the 4,5-epoxymorphinan derivative coexist with sodium thiosulfate, a sugar or a sugar alcohol. On the other hand, it has been found that degradation is facilitated by adding, for example, a binder such as polyvinyl alcohol or hydroxypropylcellulose, or a disintegrant such as croscarmellose sodium or carmellose sodium, generally used in formulation. However, the present inventors have found surprisingly that only hydroxypropylcellulose having the low degree of substitution among the disintegrants allows the 4,5-epoxymorphinan derivative or the pharmacologically acceptable acid addition salt thereof to exist stably in the solid preparation by making it coexist with sodium thiosulfate, the sugar or the sugar alcohol, and then have completed the present invention.

Accordingly, the present invention is related to the invention described below.

(1) A stable solid preparation comprising as an effective ingredient a 4,5-epoxymorphinan derivative represented by the general formula (I) or a pharmacologically acceptable acid addition salt thereof, and comprising sodium thiosulfate, a sugar or a sugar alcohol, and hydroxypropylcellulose having a low degree of substitution in an amount of 1 to 30% by weight per weight of a unit containing the effective ingredient.

(2) The stable solid preparation according to (1), wherein said sugar or sugar alcohol contains at least one selected from the group consisting of starch, saccharose, lactose, mannitol, erythritol and maltitol.

(3) The stable solid preparation according to any of (1) or (2), wherein said sugar or sugar alcohol is a granulated granule manufactured by extruding granulation, agitating granulation, spray drying or fluidized bed granulation.

(4) The stable solid preparation according to any of (1) to (3), which is obtained by a production method comprising a step of dissolving or suspending the effective ingredient in water or a pharmacologically acceptable solvent and adding to the sugar or the sugar alcohol.

(5) The stable solid preparation according to any of (1) to (4), which is a tablet, a capsule; a granule, a subtle granule or a powder.

(6) A stable solid preparation, wherein the solid preparation according to any of (1) to (5) is coated.

Effect of the Invention

The solid preparation comprising the 4,5-epoxymorphinan derivative represented by the general formula (I) or the pharmacologically acceptable acid addition salt thereof as the effective ingredient is excellent in storage property and stably contains the effective ingredient even after a long period of time has passed since its production.

BEST MODES FOR CARRYING OUT THE INVENTION

The solid preparation of the present invention is described below.

A 4,5-epoxymorphinan derivative which is the effective ingredient of the present invention is a compound represented by the general formula (I) or the pharmacologically acceptable acid addition salt thereof.

[Chemical 1]

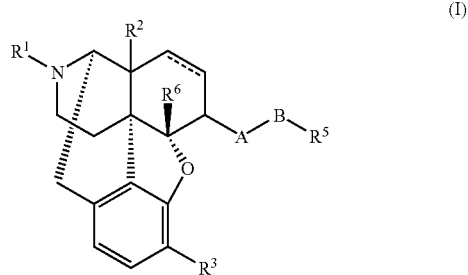

(I)

Here, in the formula (I), a double line of a dashed line and a solid line represents a double bond or a single bond; $R^1$ represents alkyl having 1 to 5 carbon atoms, cycloalkylalkyl having 4 to 7 carbon atoms, cycloalkenylalkyl having 5 to 7 carbon atoms, aryl having 6 to 12 carbon atoms, aralkyl having 7 to 13 carbon atoms, alkenyl having 4 to 7 carbon atoms, allyl, furan-2-ylalkyl having 1 to 5 carbon atoms or thiophene-2-ylalkyl having 1 to 5 carbon atoms; $R^2$ represents hydrogen, hydroxy, nitro, alkanoyloxy having 1 to 5 carbon atoms, alkoxy having 1 to 5 carbon atoms, alkyl having 1 to 5 carbon atoms or —$NR^7R^8$; $R^7$ represents hydrogen or alkyl having 1 to 5 carbon atoms; $R^8$ represents hydrogen, alkyl having 1 to 5 carbon atoms or —C(=O)$R^9$—; $R^9$ represents hydrogen, phenyl or alkyl having 1 to 5 carbon atoms; $R^3$ represents hydrogen, hydroxy, alkanoyloxy having 1 to 5 carbon atoms or alkoxy having 1 to 5 carbon atoms; A represents —$N(R^4)C(=X)$—, —$N(R^4)C(=X)Y$—, —$N(R^4)$—, or —$N(R^4)SO_2$— (wherein X and Y each independently represent $NR^4$, S or O, and $R^4$ represents hydrogen, straight or branched alkyl having 1 to 5 carbon atoms or aryl having 6 to 12 carbon atoms, and $R^4$ in the formula may be the same or different); B represents a valence bond, straight or branched alkylene having 1 to 14 carbon atoms (with the proviso that the alkylene may be substituted with at least one or more substituents selected from the group consisting of alkoxy having 1 to 5 carbon atoms, alkanoyloxy having 1 to 5 carbon atoms, hydroxy, fluorine, chlorine, bromine, iodine, amino, nitro, cyano, trifluoromethyl, trifluoromethoxy and phenoxy, and wherein 1 to 3 methylene groups may be replaced with carbonyl groups), straight or branched non-cyclic unsaturated hydrocarbon containing 1 to 3 double bonds and/or triple bonds and having 2 to 14 carbon atoms (with the proviso that the hydrocarbon may be substituted with at least one or more substituents selected from the group consisting of alkoxy having 1 to 5 carbon atoms, alkanoyloxy having 1 to 5 carbon atoms, hydroxy, fluorine, chlorine, bromine, iodine, amino, nitro, cyano, trifluoromethyl, trifluoromethoxy and phenoxy, and wherein 1 to 3 methylene groups may be replaced with carbonyl groups), or straight or branched saturated or unsaturated hydrocarbon containing 1 to 5 thioether bonds, ether bonds and/or amino bonds and having 1 to 14 carbon atoms (with the proviso that the heteroatom is not directly bound to A, and 1 to 3 methylene groups may be replaced with carbonyl groups); $R^5$ represents hydrogen or an organic group having the following basic skeleton:

Organic groups represented by $R^5$

[Chemical 2]

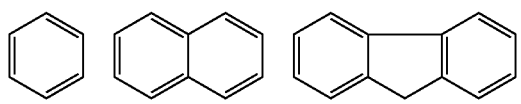

-continued

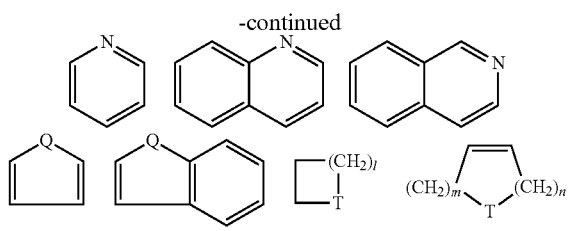

Q: N, O, S
T: CH, N, S, O
l = 0-5
m,n $\underset{\leq 5}{\geq 0}$ (with the proviso that the organic group may be substituted with at least one or more substituents selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, amino, nitro, cyano, isothiocyanate, trifluoromethyl, trifluoromethoxy and methylenedioxy); and $R^6$ represents hydrogen, alkyl having 1 to 5 carbon atoms or alkanoyl having 1 to 5 carbon atoms.

The double line of the dashed line and solid line in the general formula (I) represents the double bond or the single bond as described above, but preferably represents the single bond.

In the general formula (I), $R^1$ is preferably methyl, ethyl, propyl, butyl, isobutyl, cyclopropylmethyl, allyl, benzyl or phenethyl, and more preferably cyclopropylmethyl or allyl.

$R^2$ and $R^3$ are each independently preferably hydrogen, hydroxy, acetoxy or methoxy.

A is preferably —N($R^4$)C(=O)—, —N($R^4$)C(=O)O—, —N($R^4$)— or —N($R^4$)SO$_2$— ($R^4$ represents hydrogen, or straight or branched alkyl having 1 to 5 carbon atoms), and among them —N($R^4$)C(=O)— or —N($R^4$)C(=O)O— ($R^4$ represents hydrogen, or straight or branched alkyl having 1 to 5 carbon atoms) is preferable.

B is preferably straight alkylene having 1 to 3 carbon atoms, —CH=CH—, —C≡C—, —CH$_2$O— or —CH$_2$S—, and among them straight alkylene having 1 to 3 carbon atoms, —CH=CH— or —C≡C— is preferable.

$R^5$ is preferably hydrogen or the organic group having the following basic skeleton:

Organic groups represented by $R^5$

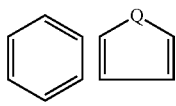

[Chemical 3]

Q = O, S (with the proviso that the organic group may be substituted with at least one or more substituents selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, amino, nitro, cyano, isothiocyanate, trifluoromethyl, trifluoromethoxy and methylenedioxy).

$R^6$ is preferably hydrogen.

The pharmacologically preferable acid addition salt may include inorganic salts such as hydrochloride salts, sulfate salts, nitrate salts, hydrobromide salts, hydroiodide salts and phosphate salts; organic carboxylate salts such as acetate salts, lactate salts, citrate salts, oxalate salts, glutarate salts, malate salts, tartrate salts, fumarate salts, mandelate salts, maleate salts, benzoate salts and phthalate salts; and organic sulfonate salts such as methanesulfonate salts, ethanesulfonate salts, benzenesulfonate salts, p-toluenesulfonate salts and camphorsulfonate salts. Among them, hydrochloride salts, hydrobromide salts, phosphate salts, tartrate salts, maleate salts and methanesulfonate salts are preferable, but certainly the salts are not limited thereto.

As the 4,5-epoxymorphinan derivative represented by the general formula (I) or the pharmacologically acceptable acid addition salt thereof in the present invention, particularly preferable are 17-(cyclopropylmethyl)-3,14β-dihydroxy-4,5α-epoxy-6β-[N-methyl-trans-3-(3-furyl)acrylamide]morphinan hydrochloride (hereinafter referred to as Compound 1) and 17-(cyclopropylmethyl)-3,14β-dihydroxy-4,5α-epoxy-6β-[N-methyl-3-(4-trifluoromethylphenyl)propiolamide]morphinan hydrochloride (hereinafter referred to as Compound 2).

[Chemical 4]

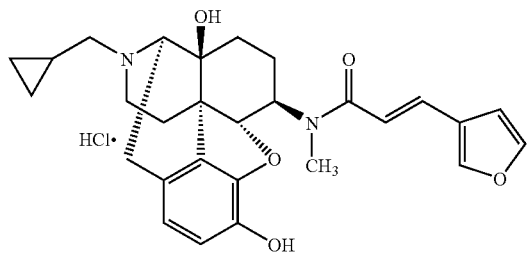

(Compound 1)

[Chemical 5]

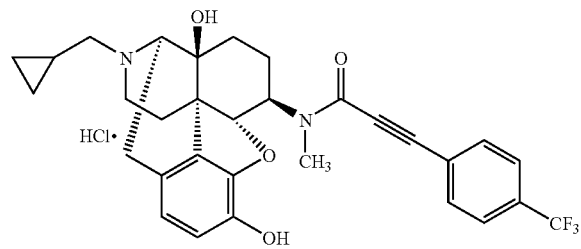

(Compound 2)

The 4,5-epoxymorphinan derivative or the pharmacologically acceptable acid addition salt thereof that is a medical ingredient of the solid preparation of the present invention can be produced, for example, by the method described in U.S. Pat. No. 2,525,552.

A blended amount of the 4,5-epoxymorphinan derivative or the pharmacologically acceptable acid addition salt thereof that is the medical ingredient of the solid preparation of the present invention is not particularly limited as long as a therapeutic effect is exerted.

For example, it can be in the range of 0.01 to 10,000 µg/preparation, and ordinarily the range of 0.1 to 1,000 µg/preparation is preferable.

As sodium thiosulfate used in the present invention, those generally commercially available may be used. Sodium thiosulfate may be an anhydride or a hydrate (pentahydrate), but is preferably the hydrate. Its blended amount may be 5% by weight or less per weight of a unit containing the effective ingredient, and is preferably 0.5% by weight or less per weight of a unit containing the effective ingredient. A lower limit of the blended amount is not particularly limited, and is ordinarily 0.00001% by weight or more per weight of a unit containing the effective ingredient. In the present invention, percent by weight per weight of a unit containing the effective ingredient means a percentage of the weight to the weight of a solid ingredient unit being directly contacted with the effective ingredient in the preparation.

As the sugar or the sugar alcohol used in the present invention, those generally Commercially available may be used. Examples of the sugar or sugar alcohol include starch, saccharose, lactose, mannitol, erythritol and maltitol, and preferably include mannitol. These specific examples can be used alone or in combination of two or more. The blended amount is not particularly limited, and is ordinarily 65% by weight or more, may be 70% by weight or more, is preferably 75% by weight or more and more preferably 80% by weight or more based on weight of a unit containing the effective ingredient in the preparation. A particle form of the sugar or sugar alcohol is not particularly limited, and is a granulated granule, powder, fine powder or the like. For example, when the solid preparation of the present invention is formulated into the tablet, the granulated granule is preferable in terms of handling. As the granulated granule, those produced by the known technique such as a spray drying, an extruding granulation, an agitating granulation or a fluidized bed granulation can be used. More preferably, a high tablet hardness is achieved without causing tableting trouble by using the spray dried granule. When a particle diameter of the sugar or sugar alcohol is small, the tableting trouble easily occurs and high tablet hardness is hardly achieved. Thus, an average particle diameter when measured according to a particle size measurement method in the 15th revised Japanese Pharmacopoeia may be 10 μm or more, is preferably 50 μm or more and more preferably 80 μm or more. An upper limit of the particle diameter is ordinarily 3,000 μm or less. The amount of the sugar or sugar alcohol to be blended in the solid preparation of the present invention can be ordinarily 65 to 99% by weight, 70 to 99% by weight, preferably 75 to 99% by weight and more preferably 80 to 99% by weight per weight of a unit containing the effective ingredient.

As hydroxypropylcellulose having the low degree of substitution used in the present invention, those generally commercially available may be used. The blended amount thereof may be 1 to 30% by weight per weight of a unit containing the effective ingredient. The average particle diameter of hydroxypropylcellulose having the low degree of substitution is preferably 10 to 300 μm and more preferably 30 to 200 μm. As a bulk density of hydroxypropylcellulose having the low degree of substitution, a loose bulk density is preferably less than 0.40 g/ml, and the lower limit thereof is generally 0.10 g/ml or more. Meanwhile, a content of hydroxypropoxyl group is preferably 10.0% by weight to 12.9% by weight. The above loose bulk density means the bulk density in the state of filling thinly, and is measured by supplying a sample into a cylindrical container (material: stainless) having a diameter of 5.03 cm and a height of 5.03 cm (volume of 100 ml) through a JIS sieve with 24 mesh from above (23 cm), flattening an upper surface and weighing the container.

Pharmacologically acceptable additives such as lubricants and coloring agents in addition to the above ingredients may be added if necessary to the solid preparation of the present invention. The lubricant include, for example, magnesium stearate, calcium stearate, talc, stearic acid, sucrose fatty acid ester and light silic anhydride.

Pharmaceutically acceptable disintegrants or binders in addition to the above ingredients may be added if necessary to the solid preparation of the present invention. For example, crystalline cellulose, hydroxypropylcellulose, partially pregelatinized starch, croscarmellose sodium and carboxymethylcellulose can also be added appropriately.

The solid preparation of the present invention can be produced using the aforementioned essential ingredients and optional ingredients (those having a role as an excipient are included in these ingredients) by the known method, and can be formulated into, for example, powders, granules, subtle granules, capsules and tablets.

The powders, the granules and the subtle granules can be produced by a wet granulation method comprising a step of dissolving or suspending the effective ingredient in water or a pharmacologically acceptable solvent and adding the solution to the sugar or the sugar alcohol. The tablets can be produced by mixing an appropriate amount of the lubricant such as magnesium stearate with the aforementioned granulated matter and compressing and molding this mixture. The capsules can be produced, for example, by filling the granulated matter in gelatin capsules. In the cases of the above production methods, sodium thiosulfate and hydroxypropylcellulose having the low degree of substitution can be added in any step. For example, sodium thiosulfate together with the effective ingredient may be dissolved or suspended in the water or the pharmacologically acceptable solvent, and added to the sugar or the sugar alcohol.

In the wet granulation, an apparatus generally used is used, and examples thereof may include a fluidized bed granulator, a rotation fluidized bed granulator, a agitating granulator, a cylindrical extruding granulator, and a wet extruding granulator. When the water is used as the solvent for dissolving or suspending the effective ingredient, the fluidized bed granulator and the rotation fluidized bed granulator capable of drying with spraying are suitable. When a volatile solvent such as ethanol as the solvent for dissolving or suspending the effective ingredient, the fluidized bed granulator, the rotation fluidized bed granulator and the agitating granulator are suitable.

As an apparatus for mixing the preparation, the apparatus generally used is used, and examples thereof may include a V-shaped mixer, a ribbon mixer, an air blender.

For the compression and molding, the apparatus generally used is used, and may include, for example, a single punch tableting machine, a rotary mode tableting machine. A molding pressure upon tableting is not particularly limited, and may be the same pressure as in usual tablets because the tablet may have the hardness to such an extent that the hardness is not problematic in handling and the tablet need not be formulated into an orally disintegrating type. Therefore, the pressure may be set to about 500 to 10,000 kgf/cm$^2$ and preferably about 1,500 to 5,000 kgf/cm$^2$.

The amount of the lubricant to be added is not particularly limited, and for example, in the case of magnesium stearate, the amount is preferably about 0.1 to 5.0% by weight and more preferably about 0.5 to 3.0% by weight per weight of a unit containing the effective ingredient.

The solid preparation comprising the epoxymorphinan derivative represented by the general formula (I) or the pharmacologically acceptable acid addition salt thereof as the effective ingredient in the present invention obtained as described above can be made into a coating preparation by adding a coating agent if necessary. The coating agent can be selected from functional bases depending on a purpose, and those such as hydroxypropylmethylcellulose, polyvinyl alcohol, ethylcellulose, carboxymethylethylcellulose or premix products thereof, which are generally commercially available, can be used. The amount of the coating agent to be added is not particularly limited, and for example, is preferably 0.1 to 20.0% by weight and more preferably 1 to 10% by weight to weight of a unit containing the effective ingredient that forms a core. Also if necessary, colcothar (iron sesquioxide), yellow colcothar (yellow iron sesquioxide), black iron oxide, titanium oxide and the like may be added as the coloring agent and a light shielding agent.

For film coating operation, the apparatus generally used is used, and a pan coating apparatus is suitable for producing film coating tablets and the fluidized bed granulator is suitable for film coating granules.

EXAMPLES

The present invention is explained below using Examples in order to clarify excellent effects of the present invention, but the present invention is not limited thereto.

Production Example 1

Comparative Example 1

10 Parts by weight (hereinafter abbreviated as a "part," and the same goes below unless otherwise specified) of the Compound 1 and 100 parts of crystalline cellulose (Avicel PH-101, Asahi Kasei) were weighed in a standard bottle, 30 parts of distilled water was added, and they were mixed by a glass bar.

Comparative Example 2

The production was performed in the same manner as in Comparative Example 1, except that crystalline cellulose in Comparative Example 1 was replaced with polyvinyl alcohol (PVA EG-5, Nippon Synthetic Chemical Industry).

Comparative Example 3

The production was performed in the same manner as in Comparative Example 1, except that crystalline cellulose in Comparative Example 1 was replaced with hydroxypropylcellulose (content of hydroxypropoxyl group: 53.4 to 77.5%, loose bulk density (apparent specific gravity): 0.5 to 0.6 g/mL, viscosity: 6.0 to 10 mPa·s (20° C., 2% aqueous solution) (HPC-L, Nippon Soda).

Comparative Example 4

The production was performed in the same manner as in Comparative Example 1, except that crystalline cellulose in Comparative Example 1 was replaced with croscarmellose sodium (Ac-di-sol, FMC Bio Polymer) (hereinafter abbreviated as Ac-di-sol).

Comparative Example 5

The production was performed in the same manner as in Comparative Example 1, except that crystalline cellulose in Comparative Example 1 was replaced with carboxymethylcellulose calcium (CMC-Ca, ECG-505, Gotoku Chemical) (hereinafter abbreviated as CMC-Ca).

Comparative Example 6

A solid preparation was produced according to the technique described in International Publication WO99/02158 Pamphlet (Patent Document 2). 49.91 Parts of lactose (Pharmatose 200M, DMV) and 26.4 parts of crystalline cellulose (Avicel PH-101, Asahi Kasei) were weighed, and placed in a fluidized bed granulator (FLO-5, Freund Corporation). A spray solution in which 0.01 part of the Compound 1, 0.08 part of sodium thiosulfate hydrate (Kokusan Chemical) and 3.2 parts of hydroxypropylcellulose (content of hydroxypropoxyl group: 53.4 to 77.5%, loose bulk density (apparent specific gravity): 0.5 to 0.6 g/mL, viscosity: 3.0 to 5.9 mPa·s (20° C., 2% aqueous solution) (HPC-SL, Nippon Soda) had been dissolved in distilled water was sprayed to the obtained granulated granules (average particle diameter of 95 μm when measured according to the particle size measurement method in the 15th revised Japanese Pharmacopoeia) to produce granulated granules. The granulated granules were treated using a comil (197S, Powrex) to obtain uniformly sized granules. 0.4 Part of magnesium stearate (Taihei Chemical Industrial) was added to 79.6 parts of the uniformly sized granules, and they were mixed for 5 minutes. The obtained granules were made into a tablet of 80 mg using a tableting machine (correct 19, Kikusui Seisakusho).

Example 1

78.895 Parts of mannitol (Pearitol SD200, Roquette Japan) was weighed and placed into the fluidized bed granulator (FLO-5, Freund Corporation) after passing through a sieve with mesh having an opening of 1 mm. A spray solution in which 0.005 part of the Compound 1 and 0.1 part of sodium thiosulfate hydrate had been dissolved in distilled water was sprayed to the obtained granulated granules (average particle diameter of 146 μm when measured according to the particle size measurement method in the 15th revised Japanese Pharmacopoeia) to produce drug-carrying granules. 15 Parts of mannitol and 5 parts of hydroxypropylcellulose having a low degree of substitution (average particle diameter: 50 μm, content of hydroxypropoxyl group: 10.0 to 12.9% by weight, loose bulk density: 0.34 g/mL, LH11, Shin-Etsu Chemical) (hereinafter abbreviated as L-HPC) were added to 79 parts of the drug-carrying granules, and they were mixed for 15 minutes using a V-shaped mixer (permeation mode S-5, Tsutsui Scientific Instruments). Further 1 part of magnesium stearate (Taipei Chemical Industrial) was added, and they were mixed for 5 minutes. The obtained granules were made into a tablet of 100 mg using the tableting machine (correct 19, Kikusui Seisakusho).

Example 2

Drug-carrying granules were produced in the same manner as in Example 1, and a tablet was made by mixing and tableting in the same manner as in Example 1, except that 10 parts of mannitol, 10 parts of L-HPC and 1 part of magnesium stearate were added to 79 parts of the Compound 1-carrying granules.

Example 3

Drug-carrying granules were produced in the same manner as in Example 1, and a tablet was made by mixing and tableting in the same manner as in Example 1, except that 20 parts of L-HPC and 1 part of magnesium stearate were added to 79 parts of the Compound 1-carrying granules.

Comparative Example 7

Drug-carrying granules were produced in the same manner as in Example 1, and a tablet was made by mixing and tableting in the same manner as in Example 1, except that 15 parts of mannitol, 5 parts of Ac-di-sol in place of L-HPC and 1 part of magnesium stearate were added to 79 parts of the Compound 1-carrying granules.

Comparative Example 8

Drug-carrying granules were produced in the same manner as in Example 1, and a tablet was made by mixing and tableting in the same manner as in Example 1, except that 10 parts of mannitol, 10 parts of CMC-Ca in place of L-HPC and 1 part of magnesium stearate were added to 79 parts of the Compound 1-carrying granules.

Example 4

68.895 Parts of mannitol (Pearitol SD200, Roquette Japan) was weighed and placed into a mortar after passing through the sieve with mesh having the opening of 1 mm. As a spray solution in which 0.005 part of the Compound 1 and 0.1 part of sodium thiosulfate hydrate had been dissolved in distilled water was sprayed, they were mixed for 5 minutes. The mixture was dried at 45° C. for 2 hours using a hot wind dryer (PS-212, ESPEC). A particle size was sorted using the comil (197S, Powrex), 30 parts of L-HPC was added, and they were mixed for 15 minutes using the V-shaped mixer (permeation mode S-5, Tsutsui Scientific Instruments). Further 1 part of magnesium stearate (Taihei Chemical Industrial) was added, and they were mixed for 5 minutes. The obtained granules were made into a tablet of 100 mg using the tableting machine (Correct 19, Kikusui Seisakusho).

Example 5

88.895 Parts of erythritol (Nikken Chemical Synthetic Industry) was weighed and placed into the mortar after passing through the sieve with mesh having the opening of 1 mm. As a spray solution in which 0.005 part of the Compound 1 and 0.1 part of sodium thiosulfate hydrate had been dissolved in distilled water was sprayed, they were mixed for about 5 minutes. The mixture was dried at 45° C. for 2 hours using the hot wind dryer (PS-212, ESPEC). A particle size was sorted using the comil (197S, Powrex), 10 parts of L-HPC was added, and they were mixed for 15 minutes using the V-shaped mixer (permeation mode S-5, Tsutsui Scientific Instruments). Further 1 part of magnesium stearate (Taipei Chemical Industrial) was added, and they were mixed for 5 minutes. The obtained granules were made into a tablet of 100 mg using the tableting machine (Correct 19, Kikusui Seisakusho).

Example 6

Granules were obtained by producing in the same manner as in Example 5, except that erythritol in Example 5 was replaced with potato starch (ST-P, Nippon Starch Chemical).

Example 7

A tablet was produced in the same manner as in Example 5, except that erythritol in Example 5 was replaced with maltitol (powder maltitol G-3, Towa Kasei).

Example 8

A tablet was produced in the same manner as in Example 5, except that erythritol in Example 5 was replaced with saccharose (Suzu Funmatsu Yakuhin).

Comparative Example 9

A tablet was produced in the same manner as in Example 4, except that the amount of blended mannitol was 58.895 parts and the amount of blended L-HPC was 40 parts.

Example 9

A tablet was produced in the same manner as in Example 5, except that erythritol in Example 5 was replaced with mannitol (Pearitol SD200, Roquette Japan).

Comparative Example 10

A tablet was produced in the same manner as in Example 5, except that erythritol in Example 5 was replaced with mannitol (Pearitol SD200, Roquette Japan) and sodium thiosulfate hydrate was not added.

Example 10

122.005 Parts of lactose (Lactose 200M, DMV), 4.2 parts of hydroxypropylcellulose (HPC-SL, Nippon Soda) and 12.25 parts of L-HPC were placed in a agitating mixing granulator (FM-VG-10P, Powrex), and mixed. Subsequently, a spray solution in which 0.005 part of the Compound 1 and 0.14 part of sodium thiosulfate hydrate had been dissolved in purified water was sprayed thereto to produce drug-carrying granules. After passing the granules through the sieve with mesh having the opening of 0.7 mm, 1.4 parts of magnesium stearate was added and mixed. The obtained granules were made into a tablet of 140 mg using the tableting machine (VIRGO 0512SS2AZ, Kikusui Seisakusho).

Examples 11 and 12

Tablets were obtained by mixing and tableting in the same manner as in Example 10, except that the amounts of blended lactose and L-HPC were changed to the amounts in Table 4.

Comparative Example 11

A tablet was obtained by mixing and tableting in the same manner as in Example 10, except that the amounts of blended lactose and L-HPC were changed to the amounts in Table 4.

(Storage Stability Test)

A stability was evaluated by measuring a residual ratio (%) of the drug using an HPLC method after the compositions, granules or tablets obtained in Comparative Examples 1 to 9 and 11 and Examples 1 to 8 and 10 to 12 were left to stand in an open state under a condition at 40° C./75% RH which was an acceleration condition described in Drug Approval and Licensing Procedure in Japan (2006) (Tables 1, 2 and 4). The stability of the tables in Example 9 and Comparative Example 10 was evaluated by measuring the amount (%) of the degraded drug after being left to stand in the open state under a condition at 60° C./75% RH that was a stress condition (Table 3).

TABLE 1

The list of the formulations and the results of storage stability test (Comparative Examples)

| Formulated ingredients | Comparative Examples | | | | | | | | |
|---|---|---|---|---|---|---|---|---|---|
| | 1 | 2 | 3 | 4 | 5 | 6 | 7 | 8 | 9 |
| Compound 1 | 9.1 | 9.1 | 9.1 | 9.1 | 9.1 | 0.0125 | 0.005 | 0.005 | 0.005 |
| Mannitol | — | — | — | — | — | — | 93.895 | 88.895 | 58.895 |
| Lactose | — | — | — | — | — | 62.3875 | — | — | — |
| Crystalline cellulose | 90.9 | — | — | — | — | 33 | — | — | — |
| L-HPC | — | — | — | — | — | — | — | — | 40 |
| PVA | — | 90.9 | — | — | — | — | — | — | — |
| Hydroxypropylcellulose | — | — | 90.9 | — | — | 4 | — | — | — |
| Ac-di-sol | — | — | — | 90.9 | — | — | 5 | — | — |
| CMC-Ca | — | — | — | — | 90.9 | — | — | 10 | — |
| Sodium thiosulfate hydrate | — | — | — | — | — | 0.1 | 0.1 | 0.1 | 0.1 |
| Magnesium stearate | — | — | — | — | — | 0.5 | 1 | 1 | 1 |
| Total | 100 | 100 | 100 | 100 | 100 | 100 | 100 | 100 | 100 |
| Residual ratio (%) of the drug after being left to stand in an open state under a condition at 40° C./75% RH for two weeks | 093.0% | 87.1% | 92.2% | 93.7% | 90.2% | — | — | — | — |
| Residual ratio (%) of the drug after being left to stand in an open state under a condition at 40° C./75% RH for one month | — | — | — | — | — | 94.4% | 93.7% | 93.0% | 96.8% |

Blended unit of formulated ingredient: indicated by percent by weight to weight of a unit of the preparation

TABLE 2

The list of the formulations and the results of storage stability test (Examples)

| Formulated ingredients | Examples | | | | | | | |
|---|---|---|---|---|---|---|---|---|
| | 1 | 2 | 3 | 4 | 5 | 6 | 7 | 8 |
| Compound 1 | 0.005 | 0.005 | 0.005 | 0.005 | 0.005 | 0.005 | 0.005 | 0.005 |
| Mannitol | 93.895 | 88.895 | 78.895 | 68.895 | — | — | — | — |
| Erythritol | — | — | — | — | 88.895 | — | — | — |
| Starch | — | — | — | — | — | 88.895 | — | — |
| Maltitol | — | — | — | — | — | — | 88.895 | — |
| Saccharose | — | — | — | — | — | — | — | 88.895 |
| L-HPC | 5 | 10 | 20 | 30 | 10 | 10 | 10 | 10 |
| Sodium thiosulfate hydrate | 0.1 | 0.1 | 0.1 | 0.1 | 0.1 | 0.1 | 0.1 | 0.1 |
| Magnesium stearate | 1 | 1 | 1 | 1 | 1 | 1 | 1 | 1 |
| Total | 100 | 100 | 100 | 100 | 100 | 100 | 100 | 100 |
| Residual ratio (%) of the compound after being left to stand in an open state under a condition at 40° C./75% RH for one month | 97.9% | 98.3% | 98.2% | 100.3% | 99.4% | 102.9% | 99.0% | 99.3% |

Blended unit of formulated ingredient: indicated by percent by weight to weight of a unit of the preparation

TABLE 3

The list of the formulations and the results of storage stability test

| Formulated ingredients | Example 9 | Comparative Example 10 |
|---|---|---|
| Compound 1 | 0.005 | 0.005 |
| Mannitol | 88.895 | 88.995 |
| L-HPC | 10 | 10 |
| Sodium thiosulfate hydrate | 0.1 | — |
| Magnesium stearate | 1 | 1 |
| Total | 100 | 100 |
| Amount of produced major degradation product (N-oxide) after the compound is left to stand in an open state under a condition at 60° C./75% RH for ten days | N.D. (<0.05%) | 0.67% |

Blended unit of formulated ingredient: indicated by percent by weight to weight of a unit of the preparation

TABLE 4

The list of the formulations and the results of storage stability test

| Formulated ingredients | Example 10 | Example 11 | Example 12 | Comparative Example 11 |
|---|---|---|---|---|
| Compound 1 | 0.0036 | 0.0036 | 0.0036 | 0.0036 |
| Lactose | 87.1464 | 78.3964 | 65.8964 | 55.8964 |
| Hydroxypropylcellulose | 3 | 3 | 3 | 3 |
| L-HPC | 8.75 | 17.5 | 30.0 | 40.0 |
| Sodium thiosulfate hydrate | 0.1 | 0.1 | 0.1 | 01 |
| Magnesium stearate | 1 | 1 | 1 | 1 |
| Total | 100.0 | 100.0 | 100.0 | 100.0 |
| Residual ratio (%) of the compound after being left to stand in an open state under a condition at 40° C./75% RH for one month | 97.6% | 98.8% | 98.8% | 96.8% |

Blended unit of formulated ingredient: indicated by percent by weight to weight of a unit of the preparation As shown in Tables 1, 2 and 4, any of the solid preparations containing sodium thiosulfate, the sugar or the sugar alcohol, and hydroxypropylcellulose having the low degree of substitution in the amount of 1 to 30% by weight per weight of a unit containing the effective ingredient exhibited the residual ratio of 97% or more even when stored without being packed under the condition at 40° C./75% RH for one month, exhibited the remarkable stabilization effect compared with the formulations in Comparative Examples, and was shown to be able to assure the sufficient stability upon handling pharmaceuticals. As shown in Table 3, no degraded product was detected in the solid preparation containing the sugar or sugar alcohol and hydroxypropylcellulose having the low degree of substitution in the amount of 1 to 30% by weight per weight of a unit containing the effective ingredient, even when the solid preparation was stored under the condition at 60° C./75% RH for 10 days. Thus, it was elucidated that sodium thiosulfate was the essential ingredient for assuring the sufficient stability during the production and the storage.

Production Example 2

Example 13

71.095 Parts of mannitol (Pearitol SD200, Roquette Japan) was weighed and placed into the fluidized bed granulator (FLO-5, Freund Corporation) after passing through the sieve with mesh having the opening of 1 mm. A spray solution in which 0.005 part of the Compound 1 and 0.1 part of sodium thiosulfate hydrate (Kokusan Chemical) had been dissolved in distilled water was sprayed thereto to produce drug-carrying granules. Subsequently, 8 parts of L-HPC (LH-11, Shin-Etsu Chemical) was added to 71.2 parts of the drug-carrying granules, and they were mixed for 15 minutes using the V-shaped mixer (permeation mode S-5, Tsutsui Scientific Instruments). Further 0.8 part of magnesium stearate (Taihei Chemical Industrial) was added, and they were mixed for 5 minutes. The obtained granules were made into a tablet of 80 mg using the tableting machine (correct 19, Kikusui Seisakusho). Subsequently, this tablet was placed in a film coating machine (High Coater Mini, Freund Corporation), and a solution in which OPADRY OY-7300 (Colorcon Japan) and iron sesquioxide (Kishi Kasei) had been dissolved or dispersed was sprayed to produce a coating tablet of 84 mg in which 4 mg of the coating agent was added to the tablet of 80 mg.

Example 14

71.0975 Parts of mannitol (Pearitol SD200, Roquette Japan) was weighed and placed into the fluidized bed granulator (FLO-5, Freund Corporation) after passing through the sieve with mesh having the opening of 1 mm. A spray solution in which 0.0025 part of the Compound 1 and 0.1 part of sodium thiosulfate hydrate (Kokusan Chemical) had been dissolved in distilled water was sprayed thereto to produce drug-carrying granules. Subsequently, 8 parts of L-HPC (LH-11, Shin-Etsu Chemical) was added to 71.2 parts of the drug-carrying granules, and they were mixed for 15 minutes using the V-shaped mixer (permeation mode S-5, Tsutsui Scientific Instruments). Further 0.8 part of magnesium stearate (Taihei Chemical Industrial) was added, and they were mixed for 5 minutes. The obtained granules were made into a tablet of 80 mg using the tableting machine (correct 19, Kikusui Seisakusho). Subsequently, this tablet was placed in the film coating machine (High Coater Mini, Freund Corporation), and a solution in which OPADRY OY-7300 (Colorcon Japan), iron sesquioxide (Kishi Kasei) and black iron oxide (Kishi Kasei) had been dissolved or dispersed was sprayed to produce a coating tablet of 84 mg in which 4 mg of the coating agent was added to the tablet of 80 mg.

Example 15

71.095 Parts of mannitol (Pearitol SD200, Roquette Japan) was weighed and placed into the fluidized bed granulator (FLO-5, Freund Corporation) after passing through the sieve with mesh having the opening of 1 mm. A spray solution in which 0.005 part of the Compound 1 and 0.1 part of sodium thiosulfate hydrate (Kokusan Chemical) had been dissolved in distilled water was sprayed thereto to produce drug-carrying granules. Subsequently, 8 parts of L-HPC (LH-11, Shin-Etsu Chemical) was added to 71.2 parts of the drug-carrying granules, and they were mixed for 15 minutes using the V-shaped mixer (permeation mode S-5, Tsutsui Scientific Instruments). Further 0.8 part of magnesium stearate (Taihei Chemical Industrial) was added, and they were mixed for 5 minutes. The obtained granules were made into a tablet of 80 mg using the tableting machine (Correct 19, Kikusui Seisakusho). Subsequently, this tablet was placed in the film coating machine (High Coater Mini, Freund Corporation), and a solution in which OPADRY 11 HP (Colorcon Japan)

and iron sesquioxide (Kishi Kasei) had been dissolved or dispersed was sprayed thereto to produce a coating tablet of 84 mg in which 4 mg of the coating agent was added to the tablet of 80 mg.

Example 16

109.7575 Parts of lactose (Lactose 200M, DMV), 4.2 parts of hydroxypropylcellulose (HPC-SL, Nippon Soda) and 24.5 parts of L-HPC (LH-31, Shin-Etsu Chemical) were placed in the agitating mixing granulator (FM-VG-10P, Powrex), and mixed. Subsequently, a spray solution in which 0.0025 part of the Compound 1 and 0.14 part of sodium thiosulfate hydrate had been dissolved in purified water was sprayed thereto to produce drug-carrying granules. After passing the granules through the sieve with mesh having the opening of 0.7 mm, 1.4 parts of magnesium stearate was added and mixed. The obtained granules were made into a tablet of 140 mg using the tableting machine (VIRGO 0512SS2AZ, Kikusui Seisakusho). Subsequently, this tablet was placed in a film coating machine (High Coater, Freund Corporation), and then a solution in which hydroxypropylmethylcellulose (TC-5, Shin-Etsu Chemical), iron sesquioxide (Kishi Kasei) and titanium oxide (Ishihara Sangyo) had been dissolved or dispersed was sprayed to produce a coating tablet of 147 mg in which 7 mg of the coating agent was added to the tablet of 140 mg.

Example 17

A tablet was produced in the same manner as in Example 16, except that the amount of the blended Compound 1 was 0.005 part and the amount of blended lactose was 109.755 parts.

(Storage Stability Test)

The stability was evaluated by measuring the residual ratio (%) of the drug using the HPLC method after the film coating tablets obtained in Examples 13 to 17 was left to stand in the open state under the condition at 40° C./75% RH that was the acceleration condition described in Drug Approval and Licensing Procedure in Japan (2006) (Table 5).

As shown in Table 5, any of the film coating tablets shown in Examples 13 to 17 containing sodium thiosulfate, the sugar or the sugar alcohol, and hydroxypropylcellulose having the low degree of substitution in the amount of 1 to 30% by weight per weight of a unit containing the effective ingredient exhibited the residual ratio of 97% or more even when stored without being packed under the condition at 40° C./75% RH for one month, and was shown to be able to assure the sufficient stability upon handling pharmaceuticals.

The invention claimed is:

1. A stable solid preparation comprising as an effective ingredient a 4,5-epoxymorphinan derivative represented by the general formula (I):

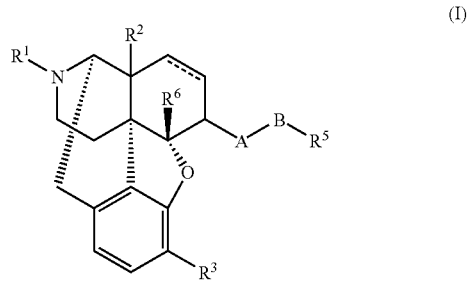

(I)

wherein in formula (I) a double line of a dashed line and a solid line represents a double bond or a single bond;

$R^1$ represents alkyl having 1 to 5 carbon atoms, cycloalkylalkyl having 4 to 7 carbon atoms, cycloalkenylalkyl having 5 to 7 carbon atoms, aryl having 6 to 12 carbon atoms, aralkyl having 7 to 13 carbon atoms, Amyl having 4 to 7 carbon atoms, allyl, furan-2-ylalkyl having 1 to 5 carbon atoms or thiophene-2-ylalkyl having 1 to 5 carbon atoms;

$R^2$ represents hydrogen, hydroxy, nitro, alkanoyloxy having 1 to 5 carbon atoms, alkoxy having 1 to 5 carbon atoms, alkyl having 1 to 5 carbon atoms or $-NR^7R^8$; $R^7$ represents hydrogen or alkyl having 1 to 5 carbon atoms; $R^8$ represents hydrogen, alkyl having 1 to 5 carbon atoms or $C(=O)R^9$; $R^9$ represents hydrogen, phenyl or alkyl having 1 to 5 carbon atoms;

TABLE 5

The list of the formulations and the results of storage stability test

| Formulated ingredients | Example 13 | Example 14 | Example 15 | Example 16 | Example 17 |
| --- | --- | --- | --- | --- | --- |
| Compound 1 | 0.005 | 0.0025 | 0.005 | 0.0025 | 0.005 |
| Mannitol | 71.095 | 71.095 | 71.095 | — | — |
| Lactose | — | — | — | 109.7575 | 109.755 |
| Hydroxypropylcellulose | — | — | — | 4.2 | 4.2 |
| L-HPC | 8 | 8 | 8 | 24.5 | 24.5 |
| Sodium thiosulfate hydrate | 0.1 | 0.1 | 0.1 | 0.14 | 0.14 |
| Magnesium stearate | 0.8 | 0.8 | 0.8 | 1.4 | 1.4 |
| Film coating | 4 | 4 | 4 | 7 | 7 |
| Total | 84 | 84 | 84 | 147 | 147 |
| Base for film coating | OPADRY OY-7300 | OPADRY OY-7300 | OPADRY II HP | Hydroxypropylmethylcellulose | Hydroxypropylmethylcellulose |
| Added dye | iron sesquioxide | iron sesquioxide black iron oxide | iron sesquioxide | titanium oxide iron sesquioxide | titanium oxide iron sesquioxide |
| Residual ratio (%) of the compound after being left to stand in an open state under a condition at 40° C./75% RH for one month | 99.4% | 99.1% | 98.3% | 98.8% | 99.5% |

It is indicated by blended amount (mg) of the formulated ingredient $R^3$ represents hydrogen, hydroxy, alkanoyloxy having 1 to 5 carbon atoms or alkoxy having 1 to 5 carbon atoms;

A represents —N($R^4$)C(=X)Y—, —N($R^4$)C(=X)Y—, —N($R^4$)—, or —N($R^4$)SO$_2$—, wherein X and Y each independently represents N$R^4$, S or O, and $R^4$ represents hydrogen, straight or branched alkyl having 1 to 5 carbon atoms or aryl having 6 to 12 carbon atoms, and $R^4$ is the same or different;

B represents (i) a valence bond, (ii) straight or branched alkylene having 1 to 14 carbon atoms, which is optionally substituted with at least one or more substituents selected from the group consisting of alkoxy having 1 to 5 carbon atoms, alkanoyloxy having 1 to 5 carbon atoms, hydroxy, fluorine, chlorine, bromine, iodine, amino, nitro, cyano, trifluoromethyl, trifluoromethoxy and phenoxy, wherein 1 to 3 methylene groups in the alkylene (ii) is optionally replaced with carbonyl groups, (iii) straight or branched non-cyclic unsaturated hydrocarbon containing 1 to 3 double bonds and/or triple bonds and having 2 to 14 carbon atoms, which is optionally substituted with at least one or more substituents selected from the group consisting of alkoxy having 1 to 5 carbon atoms, alkanoyloxy having 1 to 5 carbon atoms, hydroxy, fluorine, chlorine, bromine, iodine, amino, nitro, cyano, trifluoromethyl, trifluoromethoxy and phenoxy, wherein 1 to 3 methylene groups in the hydrocarbon (iii) is optionally replaced with carbonyl groups, or (iv) straight or branched saturated or unsaturated hydrocarbon containing 1 to 5 thioether bonds, ether bonds and/or amino bonds and having 1 to 14 carbon atoms, wherein the heteroatom in the hydrocarbon (iv) is not directly bound to A, and 1 to 3 methylene groups in the hydrocarbon (iv) is optionally replaced with carbonyl groups;

$R^5$ represents hydrogen or an organic group having the following basic skeleton:

Organic groups represented by $R^5$

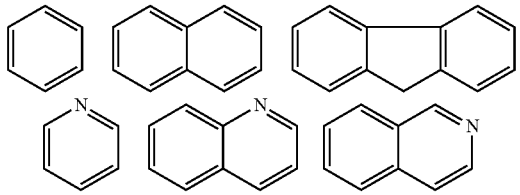

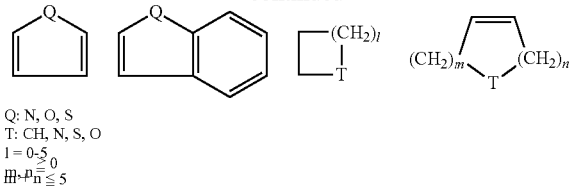

Q: N, O, S
T: CH, N, S, O
l = 0-5
$0 \leq m+n \leq 5$ wherein the organic group is optionally substituted with one or more substituents selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, amino, nitro, cyano, isothiocyanate, trifluoromethyl, trifluoromethoxy and methylenedioxy; and $R^6$ represents hydrogen, alkyl having 1 to 5 carbon atoms or alkanoyl having to 5 carbon atoms;

or a pharmacologically acceptable acid addition salt thereof; and further comprising sodium thiosulfate, a sugar or a sugar alcohol, and hydroxypropylcellulose having a low degree of substitution in an amount of 1 to 30% by weight per weight of a unit containing the effective ingredient.

2. The stable solid preparation according to claim 1, wherein said sugar or sugar alcohol contains at least one selected from the group consisting of starch, saccharose, lactose, mannitol, erythritol and maltitol.

3. The stable solid preparation according to claim 1, wherein said sugar or sugar alcohol is a granulated granule manufactured by extruding granulation, agitating granulation, spray drying or fluidized bed granulation.

4. The stable solid preparation according to claim 1, which is obtained by a production method comprising a step of dissolving or suspending the effective ingredient in water or a pharmacologically acceptable solvent to produce a solution or suspension, and a step of adding the solution or suspension to the sugar or the sugar alcohol.

5. The stable solid preparation according to claim 1, which is a tablet, a capsule, a granule, a subtle granule or a powder.

6. The solid preparation according to claim 1, wherein said solid preparation is coated.

7. The stable solid preparation according to claim 1, wherein the hydroxypropylcellulose having a low degree of substitution has a hydroxypropoxyl content of 10.0% by weight to 12.9% by weight.

* * * * *